(12) United States Patent
Nissila et al.

(10) Patent No.: US 7,361,141 B2
(45) Date of Patent: Apr. 22, 2008

(54) METHOD AND DEVICE FOR WEIGHT MANAGEMENT OF HUMANS

(75) Inventors: Seppo Nissila, Oulu (FI); Juuso Nissila, Oulu (FI); Hannu Kinnunen, Oulu (FI)

(73) Assignee: Polar Electro Oy, Kempele (FI)

( * ) Notice: Subject to any disclaimer, the term of this patent is extended or adjusted under 35 U.S.C. 154(b) by 670 days.

(21) Appl. No.: 10/637,808

(22) Filed: Aug. 8, 2003

(65) Prior Publication Data

US 2005/0004436 A1 Jan. 6, 2005

(30) Foreign Application Priority Data

Apr. 29, 2003 (FI) .................................. 20030647

(51) Int. Cl.
*A61B 5/00* (2006.01)

(52) U.S. Cl. ...................................... 600/300

(58) Field of Classification Search ................. 600/300
See application file for complete search history.

(56) References Cited

U.S. PATENT DOCUMENTS

| | | | |
|---|---|---|---|
| 4,625,733 A | | 12/1986 | Saynajakangas |
| 4,951,197 A | | 8/1990 | Mellinger |
| 5,704,350 A | | 1/1998 | Williams |
| 5,839,901 A | | 11/1998 | Karkanen |
| 5,890,128 A | | 3/1999 | Diaz et al. |
| 6,039,989 A | * | 3/2000 | Bangs et al. ................. 426/106 |
| 6,102,706 A | * | 8/2000 | Khoo et al. ................. 434/127 |
| 6,277,080 B1 | | 8/2001 | Nissilä et al. |
| 2002/0019585 A1 | | 2/2002 | Dickinson |
| 2002/0047867 A1 | * | 4/2002 | Mault et al. ................. 345/810 |
| 2002/0099274 A1 | | 7/2002 | Isomura |
| 2002/0107433 A1 | | 8/2002 | Mault |

(Continued)

FOREIGN PATENT DOCUMENTS

WO    WO 92/12490    7/1992

(Continued)

OTHER PUBLICATIONS

Jequier, E., and Tappy, L., "Regulation of Body Weight in Humans," *Physiological Review*, vol. 79, No. 2, pp. 451-480, Apr. 1999.

(Continued)

*Primary Examiner*—Robert L. Nasser, Jr.
*Assistant Examiner*—Karen E Toth
(74) *Attorney, Agent, or Firm*—Hoffman & Baron, LLP (57) ABSTRACT

The invention relates to a method and device for weight management of humans. First, the user's initial weight and his target weight are received via a user interface of the device, then food intake amount and exercise instructions to be presented via the user interface of the device are generated on the basis of the difference between the user's initial weight and his target weight. In addition, the user's energy expenditure is generated with the device and the user's food intake amount is received via the user interface of the device. Further, the user's current weight is received via the user interface and a change in the user's weight is generated with the device. Further still, the food intake amount and/or exercise instructions to be presented via the user interface of the device are modified with the device on the basis of the change in the user's weight.

34 Claims, 2 Drawing Sheets

U.S. PATENT DOCUMENTS

| | | | |
|---|---|---|---|
| 2002/0109600 A1 | 8/2002 | Mault et al. | |
| 2002/0133378 A1* | 9/2002 | Mault et al. | 705/3 |
| 2003/0065257 A1 | 4/2003 | Mault et al. | |
| 2003/0208133 A1* | 11/2003 | Mault | 600/532 |
| 2003/0219513 A1* | 11/2003 | Gordon | 426/87 |
| 2003/0226695 A1* | 12/2003 | Mault | 177/25.16 |
| 2005/0113650 A1* | 5/2005 | Pacione et al. | 600/300 |
| 2006/0015016 A1* | 1/2006 | Thornton | 600/300 |

FOREIGN PATENT DOCUMENTS

| | | |
|---|---|---|
| WO | WO 01/52718 A2 | 7/2001 |

OTHER PUBLICATIONS

Schofield, W.N., Schofield, C., and James, W.P.T., "Basal Metabolic Rate-Review and Prediction, Together with an Annotated Bibilography of Source Material", *Human Nutrition: Clinical Nutrition*, vol. 39C, Suppl. 1, pp. 1-96 (1985).

Black, A.E., Coward, W.A., Cole, T.J. and Prentice A.M., "Human Energy Expenditure in Affluent Societies: An Analysis of 574 Doubly-Labelled Water Measurements", *European Journal of Clinical Nutrition*, vol. 50, pp. 72-92 (1996).

Official Action issued in the Finnish priority Application No. 20030647.

European Search Report from European Application No. 03102440.9-2305.

European Search Report from European Application No. EP 03102440.

Official Action concerning Finnish priority application No. 20030647.

* cited by examiner

METHOD AND DEVICE FOR WEIGHT MANAGEMENT OF HUMANS

This application claims priority based in Finnish Patent Application No. 20030647; filed on Apr. 29, 2003.

FIELD OF THE INVENTION

The invention relates to a portable, personal electronic device to be used for the body weight management of a user thereof, and to a method for managing human body weight by using a portable, personal electronic device.

BRIEF DESCRIPTION OF THE RELATED ART

There are innumerable known methods, devices, nutritive preparations and drugs for weight management of humans.

The Applicants are of the opinion that the best scientific basis for weight management is provided by energy balance control based on laws of thermodynamics, i.e. a person's energy expenditure is compared with the energy content of his food intake amount. If they are in balance, the person's weight remains unchanged. If the person's energy expenditure is greater than the energy content of his food intake, the person loses weight. If the energy content of the amount of food eaten by the person is greater than his energy expenditure, he gains weight. Management of energy balance is described in greater detail in Jéquier, E. and Tappy, L: *Regulation of Body Weight in Humans. Physiol. Rev.* 79:451-480, 1999, which is incorporated herein as a reference.

US Patent Application 2002/0,019,585, also incorporated herein as a reference, discloses a wrist-worn device for monitoring the management of energy balance. The use of this kind of device may, however, involve problems caused by incorrectly estimated energy expenditure of the user, or incorrect food intake amounts entered by the user by mistake. As a result, the management of the user's energy balance may fail.

SUMMARY OF THE INVENTION

It is an object of the invention to provide an improved, portable personal electronic device for the body weight management of a user thereof.

As an aspect of the invention there is provided a portable, personal electronic device for the body weight management of a user thereof, comprising: a control unit for controlling the device; and a user interface coupled to the control unit for entering input information and for obtaining output information, the control unit being configured to receive an initial weight, a target weight and food intake amount of the user via the user interface, to generate the energy expenditure of the user, to generate food intake amount and exercise instructions based on the difference between the user's initial weight and his target weight for display via the user interface, to receive the user's current weight via the user interface, to generate a change in the user's weight, and to modify on the basis of the change in the user's weight the food intake amount and/or exercise instructions to be displayed via the user interface.

It is an object of the invention to provide a method for managing body weight by using a portable, personal electronic device.

As an aspect of the invention there is provided a method for managing human body weight by using a portable, personal electronic device, the method comprising: receiving an initial weight and a target weight of a user via a user interface of the device; generating food intake amount and exercise instructions based on the difference between the user's initial weight and his target weight for display via the user interface; generating with the device the user's energy expenditure; receiving the user's food intake amount via the user interface; receiving the user's current weight via the user interface of the device; generating with the device a change in the user's weight; and modifying with the device the food intake amount and/or exercise instructions to be displayed via the user interface on the basis of the change in the user's weight.

The invention is based on the idea of modifying the instructions on food intake amounts and/or exercise on the basis of the change in the user's weight.

The method and device of the invention provide a number of advantages. The device makes weight management more efficient and accurate than before, because the device calibrates itself automatically, which eliminates the impact of errors caused by the user and any errors possibly appearing in the default settings made by the device. The calibration takes place as follows: if it is observed that weight management (or weight change) is not leading to the planned result, the device corrects and adjusts the instructions it has issued such that any incorrect input data entered by the user or levels of input data and conclusions drawn from these will be amended.

BRIEF DESCRIPTION OF THE DRAWINGS

In the following the invention will be described in greater detail in connection with the preferred embodiments and with reference to the accompanying drawings, in which.

DETAILED DESCRIPTION OF THE PREFERRED EMBODIMENTS

Figure 1:
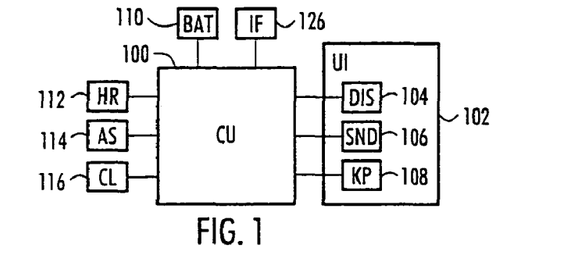
FIG. 1 is a schematic block diagram illustrating the components of a portable, personal electronic device to be used for the body weight management of a user thereof.

With reference to FIG. 1, the structure of a portable, personal electronic device for the body weight management of a user thereof is described in a suitably simplified manner. The device comprises a control unit 100 for controlling the device and a user interface 102 coupled to the control unit 100 for entering input information and for obtaining output information. The device is provided with an independent power source 110, such as a battery or a rechargeable accumulator. A solar cell to be coupled to the device or fixedly attached thereto for producing current from a light source can also be used for generating power. There are also other known methods that may be used for generating power for the portable device, for example a small power generator, manufactured by watchmaker Seiko®, which generates power from motion.

The control unit 100 is usually implemented as a processor provided with the necessary software, although different hardware implementations are also possible, such as a circuit made of separate logic components or one or more Application-Specific Integrated Circuits (ASIC). One example of a processor that can be used is Seiko-Epson® 8-byte microprocessor, type S1C8F. If necessary, a plural number of processors can also be used. A hybrid of these different implementations is possible as well. When selecting the implementation, a person skilled in the art will take into account the requirements set to the size and power consumption of the device, the required processing power and memory capacity, the manufacturing costs involved and production volumes.

The user interface 102 of the device typically comprises a display 104, a sound reproduction means 106, and a keypad 108. The display may be a liquid crystal display, for example, but it may also be implemented using any suitable display technology known in the prior art. The sound reproduction means 106 may be a loudspeaker or a simpler device, such as a pietzo crystal producing beeps, for example, or other sound signals. The keypad 108 may even comprise a complete qwerty set of keys, a numerical keypad alone, or only some push buttons and/or turn buttons. In addition, the user interface 102 may comprise other prior art user interface elements, such as different cursor pointing devices (a mouse, a trackball, different arrow keys, etc.), or elements enabling audio control.

The control unit 100 is configured to receive the user's initial weight and his target weight over the user interface 102. The weights can be expressed for example in kilograms, pounds, or in some other weight measurement units. The weight is given at an accuracy of one kilogram, although a better accuracy is preferred, such as an accuracy of 0.3 or 0.1 kg. The user obtains his initial weight by weighing himself on scales, for example.

When selecting his target weight, the user decides whether he wishes to maintain his current weight or to lose weight. Since the device is designed for the mass market and since weight increase is usually not preferred, the possibility of the user setting a target weight that is higher than his current weight can be been prevented in the device. In addition, since gradually proceeding weight loss is best as regards both efficiency and health, the device may be set to prevent the target weight from being set at a level lower than 90% of the initial weight.

The target weight can also be checked against the BMI (Body Mass Index) of the user. BMI is arrived at by dividing the user's weight in kilograms by his height in metres squared. For example, if the user is 1.72 metres tall and his (initial) weight is 69.0 kilograms, his BMI is $69,0/(1.72)^2=23.3$. The control unit 100 can be configured to receive the user's height over the user interface 102 and BMI can then be calculated in the control unit 100. BMI is generally interpreted as shown in Table 1. The control unit 100 can thus be configured not to allow the user to set his target weight to a level that would reduce his BMI to less than 18.5.

TABLE 1

| | |
|---|---|
| Underweight | BMI < 18.5 |
| Normal weight | 18.5 ≦ BMI < 25 |
| Overweight | 25 ≦ BMI < 30 |
| Obesity | BMI ≧ 30 |

The control unit 100 is configured to receive the user's food intake amount via the user interface 102. The control unit 100 can be configured to process the food amounts in terms of their energy contents. The user can thus enter his food intake amount in calories or joules or in some other energy measurement units. Today the most typical unit for expressing energy content is kilocalorie or kilojoule. The device can also be designed and constructed such that the user enters the food intake amount by specifying the food items, such as "one doughnut", in which case the device contains a database stored therein for converting the food intake amount into energy content. The food intake amount can also be entered as points, such as those used by the Weight Watchers®.

The control unit 100 is configured to generate the user's energy expenditure, which is preferably determined using the same unit of measurement that was used for expressing the user's food intake amount, i.e. calories or joules. Other suitable measurement units can also be used and, when necessary, conversion formulae are devised to enable the comparison between the energy expenditure and the energy content of the food intake amount. The user's energy expenditure can be generated using prior art methods. In the following, embodiments based on the user's heart rate, physical activity, basal metabolism, and his workload will be described. These may also be combined for more accurate generation of energy expenditure for example as follows: when the user is exercising, his heart rate is measured, whereas at other times his physical activity is measured, in addition to which information about his basal metabolism is taken into account, and possibly information about his workload.

Figure 2:
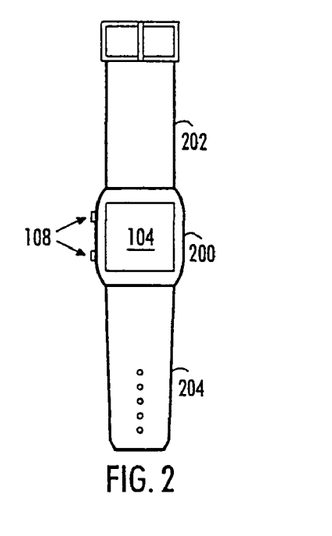
FIG. 2 is a wrist-worn measuring device.

The device may be a part of a measuring device that measures energy expenditure caused by physical exercise. The device may also be a sports watch designed to serve as an auxiliary device in sports, hiking, sailing, mountain climbing and/or snow sports. According to an embodiment, the device further comprises a rate measuring unit 112 coupled to the control unit 100 and measuring the user's heart rate. When generating the user's energy expenditure, the control unit 100 is configured to take into account the measured heart rate of the user. The device illustrated in FIG. 1 may thus be a wrist-worn measuring device like the one shown in FIG. 2, for example. The wrist-worn measuring device comprises electronics components described in connection with FIG. 1, such as the keys 108 and the liquid crystal display 104 shown in FIG. 2, which are protected by a (usually watertight) cover 200. The wrist-worn measuring device further comprises a wristband 202, 204 for fastening the device to the wrist.

The device may thus be a heart rate monitor used for monitoring the user's heart rate and possibly other non-invasively measurable parameters (such as blood pressure). In U.S. Pat. No. 4,625,733, which is incorporated herein as a reference, Säynäjäkangas describes a wireless and continuous heart rate measurement concept in which a transmitter attached to the user's chest measures the user's heart rate at the accuracy of EKG (electrocardiogram) and transfers the heart rate data telemetrically by means of magnetic coils to a heart rate receiver attached to the user's wrist. Instead of using a transmitter/receiver-type solution, a heart rate monitor may be implemented by measuring heart rate directly from the wrist on the basis of pressure, for example. Also other prior art heart rate measuring methods may be used, provided that they are applicable for use in a portable, personal electronic device designed for the body weight management of its user.

Polar Electro® (web site at the address: www.polar.fi) designs and manufactures heart rate monitors that comprise an electrode transmitter belt to be fastened around the chest and a wrist-worn device which is the actual heart rate monitor. The electrode transmitter belt has an electronics unit for receiving heart rate information from electrodes that measure one or more heart rate information parameters. From the electrodes a signal is supplied to an EKG preamplifier, then transferred to an AGC (Automatic Gain Control) amplifier and, through a power amplifier, further to the transmitter. The transmitter may be implemented in the form of a coil transmitting the heart rate information inductively to the receiver. One heartbeat corresponds to one burst of 5 kHz, for example, or to a group of several bursts. Information may be transmitted inductively or by other suitable prior art data transmission means, such as radio carriers, optically or through a conductor. The receiver of the actual heart rate monitor may be implemented in the form of a receiver coil from which the received signal is supplied through a signal receiver to the control unit 100, which controls and coordinates the operation of the different parts of the heart rate monitor. The heart rate monitor often comprises an interface 126 between the monitor and the outside world. Through the interface 126 data stored in the heart rate monitor may be transferred to a personal computer, for example, for further processing. In addition, the software of the heart rate monitor may be updated over the interface 126.

The control unit 100 may be configured to generate an index representing the aerobic fitness of the user based on the user's current weight, height, age and gender. Aerobic fitness corresponds to cardiovascular fitness (a measurement unit for describing oxygen uptake, usually 10-95 millilitres/kilogram/minute). At a particular exercise heart rate, the energy expenditure (in addition to basal metabolism) of a person who is in a poor physical condition is 33% lower than that of a person who is in normal condition. On the basis of material obtained from laboratory measurements of different test persons, the Applicant has devised a method for estimating aerobic fitness based on the above user parameters. The control unit 100 may be configured to receive the user's resting heart rate and his maximum heart rate over the user interface 102. If the user does not know these values, they can be estimated as follows: the resting heart rate is 55 beats per minute and the maximum heart rate is arrived at by subtracting the user's age in years from 220. On the basis of aerobic fitness, resting heart rate, and maximum heart rate, energy expenditure caused by physical exercise can be estimated, which in turn has an influence on the exercise instructions.

According to an embodiment, the device further comprises an activity unit 114 coupled to the control unit 100 and measuring the physical activity of the user. When generating the user's energy expenditure, the control unit 100 is configured to take into account the measured physical activity of the user. The activity unit 114 can be implemented by means of a sensor measuring the user's activity. The sensor may be an acceleration sensor, for example, placed into the device. One of the following acceleration sensors, for example, may be used: Analog Devices ADXL105, Pewatron H W or VTI Technologies SCA-series. In a wrist-worn measuring device the activity unit 114 is thus placed to the user's wrist, where it measures the movements of the hand. The signals coming from the activity unit 114 are analysed in the control unit 100. The user's physical activity can be identified on the basis of the signals. Physical activity can be determined as different states, such as: resting, standing, walking and running. Each state can be expressed by means of the user interface 102, for example by showing the name of the state on the display 104. Physical activity can be turned into an index, such as an activity index for 24 h, which can be shown to the user on the display 104. The monitoring of physical activity may help the user to avoid a drop in physical activity, which often happens during a weight loss process, because reduction in the food intake amount may lead to instinctive reduction of physical activity.

According to an embodiment, the control unit 100 is configured to receive information defining the user's age over the user interface 102. This information may consist of the user's age, in years, or his birthday. In the latter case the device must contain a calendar from which the current date can be obtained and thus the user's age can be calculated by determining the length of the period from the user's birthday to the current date. According to this embodiment, the control unit 100 is further configured to take into account the user's basal metabolic rate (BMR), defined on the basis of his age and weight, when generating the user's energy expenditure. BMR can be estimated using formulae devised by the WHO (World Health Organization) for this purpose. The calculation of BMR is described in an article, *Schofield W. N., Schofield, C, and James, W. P. T., "Basal Metabolic Rate—Review and Prediction, Together with an Annotated Bibliography of Source Material", Human Nutrition: Clinical Nutrition, Vol.* 39C, *Suppl.* 1, pp. 1-96, (1985), incorporated herein as a reference. The accuracy of BMR can be improved by taking into account the user's gender, which can be entered into the control unit 100 via the user interface 102. BMR is 10-15% lower for women than for men.

According to an embodiment the control unit 100 is configured to receive over the user interface 102 information defining the user's workload and to take the user's workload into account when generating his energy expenditure. One way of measuring workload is to use working day descriptions for estimating daily energy expenditure. Working day descriptions may contain three activity categories: seated work, seated work with requirement of moving around, and standing work. Seated work expends 12.5% less energy per day than seated work with requirement of moving around. Standing work, in turn, expends 12.5% more energy than seated work with requirement of moving around. For a male weighing 75 kilograms, for example, a difference of 12.5% equals 2450 kilocalories per week, which means a potential increase or loss of weight of 0.35 kilograms in a week. The use of working day descriptions is discussed in an article by Black A E, Coward W A, Cole T J, and Prentice A M: Human energy expenditure in affluent societies: an analysis of 574 doubly-labelled water measurements. *Eur J Clin Nutr* 50, 72-92, 1996, incorporated herein as a reference.

On the basis of the difference between the user's initial weight and his target weight, the control unit 100 is configured to generate food intake amount and exercise instructions for display via the user interface 102. According to an embodiment the food intake amount instructions comprise a recommended energy content of a daily food intake amount. According to an embodiment the exercise instructions comprise recommended weekly exercise energy.

According to an embodiment the user can set a desired length for the weight management program over the user interface 102. If the user wishes to lose weight, for example, he can select a weight reduction program and set its duration at three months and then change to a weight maintenance program. For reasons of safety, the control unit 100 may be configured to change the duration of the program set by the user. A weight reduction program may contain a restriction that allows the energy content of the user's food intake amount to be reduced by not more than 20-40% from the normal. For a male of 75 kilograms, 30% could equal to 650 kilocalories per day. It is also possible to restrict the total duration of the program to six months, for example.

According to an embodiment the user may set a desired exercise amount via the user interface 102. The options for the exercise amount may be determined by a verbal description: low, moderate, high. In addition, training duration (for example at 50% efficiency in relation to the maximum heart rate) can be adjusted in hours, for example.

Figure 3:
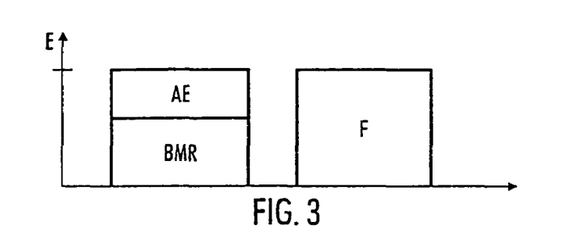
FIG. 3 illustrates how weight is kept stable by balancing energy expenditure and the energy amount of food intake.

FIG. 3 illustrates a case in which the initial weight and the target weight set by the user are the same. The aim is thus to maintain the current weight. The vertical axis represents energy given in kilocalories. The column on the left-hand side shows the user's energy expenditure, which comprises basal metabolic rate BMR and energy expenditure AE during ordinary activity and standard exercising. The right-hand side column shows the energy content F of the user's food intake amount. The user is thus given exercise and food intake amount instructions that allow energy expenditure and the energy intake amount to be kept in balance, whereby the user's weight remains unchanged.

According to an embodiment the control unit 100 is configured to inform via the user interface 102 the energy content of the food amount consumed within a predetermined period. At the same time the allowed total energy content determined for said predetermined period and/or the difference between said total energy content and said energy content of the food amount consumed are informed. This allows the user to easily monitor his consumption of the energy amount provided by the food intake amount instructions and/or the amount of energy still left. The most natural duration for the predetermined period is 24 hours, but periods of a different duration can also be used, when necessary.

According to an embodiment the control unit 100 is configured to inform via the user interface 102 the amount of energy expended in an exercise carried out within a predetermined period, the target exercise energy expenditure set for said predetermined period, and/or the difference between said target exercise energy expenditure and said expended energy amount. This embodiment allows the user to monitor the amount of exercising he has already carried out (expressed as energy expenditure or as training time) to expend the energy amount required by the exercise instructions. It can also be used to show how much more exercising would be needed to reach the target. Here a suitable duration for the predetermined period is one week, but periods of different durations, such as 24 hours, several weeks, or one month, can also be applied, when necessary.

Figure 4:
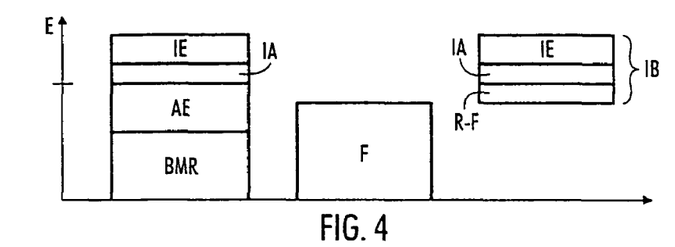
FIGS. 4, 5 and 6 illustrate weight loss based on reducing the amount of energy in the food intake amount and on increasing energy expenditure, FIG. 4 illustrating a weight reduction plan, FIG. 5 weight loss follow-up data, and FIG. 6 a weight reduction plan modified on the basis of the follow-up data.

FIG. 4 illustrates a case in which the target weight set by the user is lower than his initial weight, i.e. the purpose is to lose weight. Weight loss is obtained through a negative energy balance IB, which is achieved as a combination of three different factors. It is possible to apply one factor or more than one at a time, but the best result is naturally obtained when all the three factors are applied simultaneously. The three factors are: energy expenditure IE due to exercising, energy expenditure IA due to increased activity, and reduced energy amount RF of food intake. In this embodiment, the control unit 100 is configured to determine for the user food intake instructions providing a daily food intake amount having an energy content that is lower than the user's daily energy expenditure and exercise instructions that increase the user's energy expenditure.

The control unit 100 is further configured to receive the user's current weight via the user interface 102, to generate a change in the user's weight, and to modify on the basis of the weight change the food intake amount and/or exercise instructions to be displayed via the user interface 102. The user obtains his current weight by weighing himself on scales, for example. According to an embodiment the control unit 100 is configured to generate the change in the user's weight on the basis of the user's current weight and his initial weight or current weight received and stored previously. According to an embodiment, the control unit 100 is configured to generate a long-term average of the change in the user's weight, the average being taken into account when food intake amount instructions and exercise guidance are generated. The duration of a monitoring period used for producing the average may be 1 to 4 weeks, for example.

According to an embodiment, the control unit 100 is configured to remind the user via the user interface 102 to enter his current weight into the device via the user interface 102. In that case the device could also comprise a clock 116 to allow the actual time of the day to be shown on the display 104. A separate clock circuit 116 is not necessarily needed, because in a control unit 100 consisting of a processor and the associated software, for example, the clock can be implemented by generating the time of the day by means of software by counting the processor clock cycles on the basis of interruptions. Improved accuracy of weight management is obtained if the user is asked to enter his current weight into the device daily at the same time, preferably in the morning.

According to an embodiment the control unit 100 is configured to generate a long-term average of the user's physical activity, the average being taken into account when food intake amount and exercise instructions are generated. In other words, in this embodiment factors AE and IA described in FIG. 4 are in practice monitored by using the activity unit 114 shown in FIG. 1, for example. The monitoring period may be 1 to 4 weeks, for example.

The change in the user's weight and the monitoring data form the basis for making conclusions on how the default presumptions have been realized and on the correctness of the information entered by the user. Next, three simple rules will be put forward, although it is to be understood that on the basis of the principles presented above, a person skilled in the art may also deduce other rules by applying his ordinary working methods. There may thus be various rules and they may be applied together or separately, depending on the situation.

Figure 5:
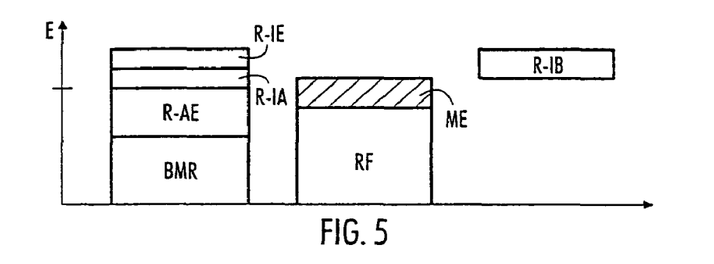

FIG. 5 illustrates the realization of the instructions described in connection with FIG. 4. Comparison of FIGS. 4 and 5 shows that the user's basic metabolic rate BMR was correctly estimated. Likewise, the above described energy expenditure monitoring methods show that the actual energy expenditure relating to ordinary activity and to standard exercising R-AE and the actual energy expenditure due to increased activity R-IA correspond to the plan, whereas the actual energy expenditure due to exercising R-IE is lower than the planned level IE. The actual energy content of the user's food intake amount RF seems to correspond to the planned level F. However, the weight loss achieved during the monitoring period and the actual negative energy balance R-IB determined on the basis thereof are much lower than the planned level IB. It can thus be concluded that the food intake amount entered into the device by the user and hence the energy content of the food intake amounts contain a systematic error ME.

Figure 6:
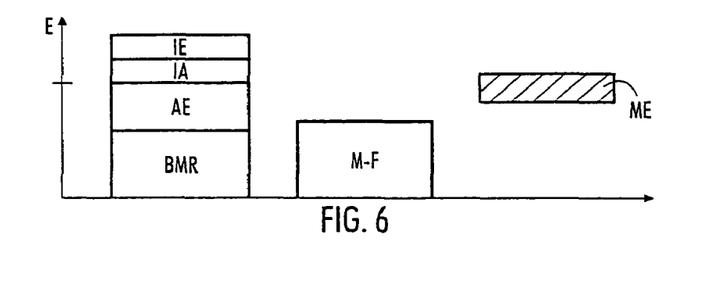

As shown in FIG. 5, the actual measured change in the user's weight provides information about the realization of the weight management. It can be used for estimating reasons for the deviations and for modifying the food intake amount and/or exercise instructions to allow weight management to be continued so that it corresponds better to the plan. In our example, we can proceed as shown in FIG. 6. The planned energy expenditure of the user shown by the column on the left-hand side does not need to be changed. It is to be noted that the amount of energy expenditure due to exercising IE does not need to be increased, whereas it is necessary to provide exercise instructions ensuring that the energy amount in question will be actually expended. Compared with the initial level exercise instructions of FIG. 4, in practice the exercise duration and/or efficiency must be increased in the situation shown in FIG. 6. The energy content of the user's food intake amount M-F depicted by the right-hand side column is changed: it is reduced by an amount equal to the measurement error ME from level F in FIG. 3.

FIGS. 4, 5 and 6 thus illustrate a first rule and according to an embodiment based on the rule, if the user's weight changes less than what was estimated on the basis of the user's food intake amount and his energy expenditure, the control unit 100 is configured to reduce the energy content of the food intake amount instructions and/or to increase the energy expenditure of the exercise instructions.

In an embodiment based on a second rule, if the user's weight changes more than what was estimated on the basis of the user's food intake amount and his energy expenditure, the control unit 100 is configured to increase the energy content of the food intake amount instructions and/or to reduce the energy expenditure of the exercise instructions.

In an embodiment according to a third rule, if the change in the user's weight corresponds to the estimate made on the basis of his food intake amount and his energy expenditure, the control unit 100 is configured to maintain the energy content of the food intake instructions and the energy expenditure of the exercise instructions at their previous level.

The modifying of the food intake amount and/or exercise instructions can be thought of as calibration of the device designed for the user's body weight management. The calibration preferably takes place in relatively small steps to avoid extreme variation of the weight management program from heavy to light. The degree of the calibration can be adjusted according to the duration of the monitoring period. For example, if the calibration is only carried out once a week, the change to be made to the food intake amount and exercise instructions may be greater than in connection with daily calibration. Since weight management programs preferably continue for months, the described procedure allows good measurement accuracy to be obtained by calibration carried out during the first few weeks. A significant advantage of the described procedure is that it adjusts to the user's habits, for example to his way of entering the food intake amounts. Even if they contained (usually a systematic) error, the calibration cancels its influence.

According to an embodiment the control unit 100 is configured to prevent the energy content of the food intake amount instructions from being decreased to a level that is too low and the amount energy expended by the exercise instructions from being increased to a level that is too high. This embodiment particularly enhances the safety of weight loss and its long-term effects. In the long run, it is not good for the user's health if he eats too little in relation to his energy expenditure. The device does not support the use of extreme, usually unhealthy, diets either. Suitable limits could be set for example at seven hours of weekly exercise at medium intensity and a negative energy balance of not more than 40% of the daily energy expenditure.

Figure 7:
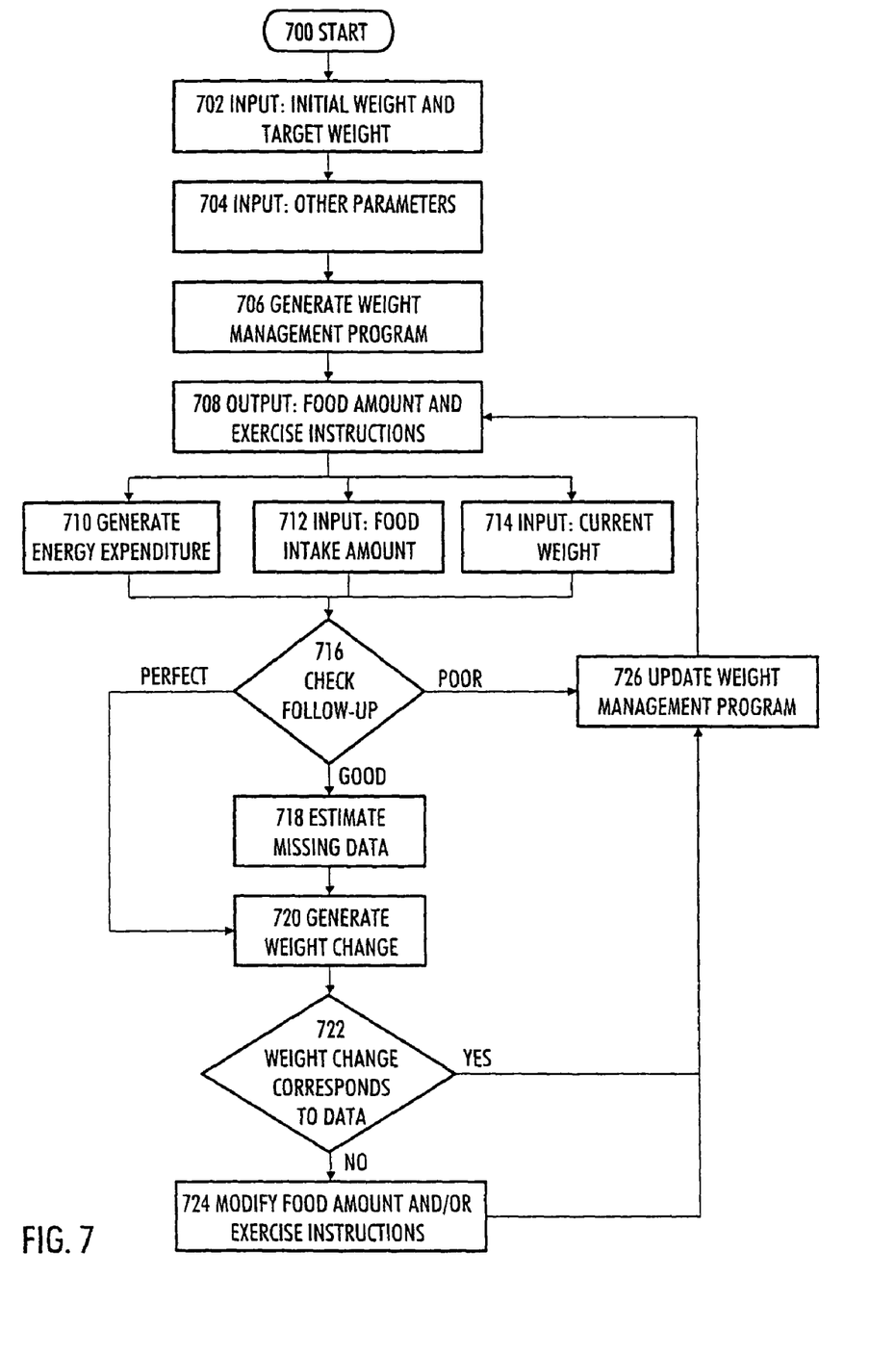
FIG. 7 is a flow chart illustrating a method for human body weight management by using a portable, personal electronic device.

With reference to FIG. 7, a method for human body weight management by using a portable, personal electronic device will be discussed. The execution of the method starts at 700 by selecting and starting a new weight management program, for example, via the user interface of the device.

Next, in 702, the user's initial weight and target weight are received over the user interface of the device.

In block 704, other parameters entered by the user may be received via the user interface of the device. The parameters were already mentioned in the description of the device, i.e. they contain at least one of the following: height, resting heart rate, maximum heart rate, information defining age, gender, information defining workload, duration of the weight management program, and the desired amount of exercise.

Next, in 706, a weight management program based on the input information and the internal logic of the device can be generated, as described above in connection with the description of the device.

In accordance with the weight management program and based on the difference between the user's initial weight and his target weight, food intake amount and exercise instructions are generated in 708 for display over the user interface of the device. According to an embodiment, the method comprises the following inference: if the user's target weight is lower than his initial weight, the device is set to generate for the user food intake amount instructions that provide a daily energy content which is lower than the user's daily energy expenditure and exercise instructions which increase the user's energy expenditure. According to an embodiment the food intake amount instructions comprise a recommended daily energy content of the food intake amount. According to an embodiment the exercise instructions comprise recommended weekly exercise energy expenditure.

After block 708 the method is divided into blocks that are executed in parallel: in block 710 the device is used for generating the energy expenditure of the user, in 712 the food intake amount of the user is received via the user interface of the device, and in 714 the user's current weight is received via the user interface. As regards the frequencies at which these blocks are executed, reference is made to the above embodiments relating to the device. Although the device processes food amounts as energy contents, food amount can be entered either according to its energy content or to some other data, for example by specifying the food item, on the basis of which its energy content can then be calculated or retrieved from the database of the device.

According to an embodiment the method further comprises: reminding the user via the user interface to enter his current weight into the device via the user interface.

According to an embodiment the method further comprises: informing via the user interface the energy content of the food intake amount for a predetermined period and the allowed total energy content determined for said predetermined period and/or the difference between said total energy content and the energy content of said food intake amount.

The user's energy expenditure can be generated by applying the embodiments described with reference to the device. According to an embodiment the method further comprises: taking into account the user's heart rate measured with the device when generating his energy expenditure. According to an embodiment the method further comprises: taking into account the user's physical activity when generating his energy expenditure. According to an embodiment the method further comprises: generating with the device a long-term average of the user's physical activity, which is taken into account when food intake amount and exercise instructions are generated. According to an embodiment the method further comprises: receiving via the user interface of the device information defining the user's age and taking into account the user's basic metabolic rate defined on the basis of his age and weight when generating the user's energy expenditure. According to an embodiment the method further comprises: receiving over the user interface of the device information defining the user's workload and taking the user's workload into account when generating his energy expenditure.

According to an embodiment the method further comprises: informing via the user interface of the device the amount of energy expended during an exercise within a predetermined period and the target exercise energy expenditure set for the predetermined period and/or the difference between said target exercise energy expenditure and said expended energy amount.

At predetermined intervals, for example daily, weekly, or at some other frequency, the quality of monitoring is checked at 716. If the user has used the device regularly for generating his energy expenditure and entered meticulously his food intake amounts, the monitoring can be considered perfect and the routine may proceed directly to 720. If the device has not been used all that meticulously but still sufficiently well, the routine may proceed to block 718, where missing data is estimated. If the use of the device is considered to be poor, the routine proceeds from block 716 to block 726. Quality can be considered perfect at 90-100% use, good at 60-90% use and poor at less than 60% use, for example.

The estimation in block 718 may be carried out for example by generating an average trend of the current weights entered by the user during a monitoring period, such as one week, and thus, if there is a day when no current weight is entered, this does not cause problems. A minimum number of values with which the calculation can be carried out could be four entered current weight values, for example. Similarly, the user's weekly food intake amount can be estimated for example by replacing one missing entry with the entry made on the previous day or by an average generated over a week, for example. In other words, if there is one day when the user has not entered the food intake amount, it is still assumed that he has eaten on that day.

As stated, the routine enters block 720 from 716, if the monitoring quality is perfect, and from 718, if estimation is carried out. In block 720 the change in the user's weight is generated with the device. When block 720 is executed for the first time, the change in the user's weight is generated with the device on the basis of the user's current weight and his initial weight. After that it is based on the user's latest current weight and the user's current weight received and stored earlier (the weight at the end of the previous monitoring period).

In block 722 the routine checks whether the change in the user's weight corresponds to the ratio of the energy expenditure, generated in 710, to the food intake amounts, entered in 712 (also taking into account missing data, if any, estimated in 718).

If the comparison made in block 722 produces a negative result, the routine proceeds to 724, where the device is used for modifying on the basis of the change in the user's weight the food intake amount and/or exercise instructions to be displayed via the user interface of the device, and if not, the routine proceeds to 726, where the weight management program is adjusted.

The calibration of the method in block 724 can be carried out in various ways. According to an embodiment, the method further comprises: reducing with the device the energy content of the food intake amount instructions and/or increasing the energy expenditure of the exercise instructions, if the change in the user's weight is smaller than estimated on the basis of the user's food intake amount and his energy expenditure. According to an embodiment the method further comprises: increasing with the device the energy content of the food intake amount instructions and/or decreasing the energy expenditure of the exercise instructions, if the change in the user's weight is greater than estimated on the basis of the user's food intake amount and his energy expenditure. According to an embodiment, the method further comprises: maintaining with the device the energy content of the food intake amount instructions and the energy expenditure of the exercise instructions on their previous level, if the change in the user's weight corresponds to the estimation made on the basis of the user's food intake amount and his energy expenditure. According to an embodiment the method further comprises: generating with the device a long-term average of the change in the user's weight, the average being taken into account when food intake amount and exercise instructions are generated. According to a further embodiment the method further comprises: preventing with the device the energy content of the food intake amount instructions from being reduced to a level that is too low and the energy expenditure of the exercise instructions from being increased to a level that is too high.

As stated, in block 726 the weight management program is updated, for example by adjusting the speed of the program, whereas block 724 calibrates the weight management program. For example, if the weight loss has taken place at the planned rate, no action needs to be taken in 726. On the other hand, if weight loss has been too rapid, the negative energy balance can be reduced in 726, and if weight loss has been too slow, the negative energy balance can be increased in 726. Realism and safety must naturally be always ensured.

From block 726 the routine proceeds to block 708, where the user is shown the food intake amount and exercise instructions modified, if necessary, in block 724.

The termination of the execution of the method is not specifically shown in FIG. 7, but it can be terminated when the user so wishes or when the period of the weight management program ends, for example after 1 to 6 months from its start.

The method can be implemented by means of a device similar to the one described earlier, which may constitute for example a part of a measuring device measuring energy expenditure in physical exercise, such as a heart rate monitor, although a person skilled in the art can also apply the above described method to other kinds of devices designed for the management of the weight of the user.

Although the invention is described above with reference to an example illustrated in the accompanying drawings, it is obvious that the invention is not restricted thereto, but can be modified in many ways within the scope of the accompanying claims.

The invention claimed is:

1. A portable, personal electronic device for body weight management of a user thereof, comprising:
   a control unit adapted to control the device; and
   a user interface coupled to the control unit adapted to enter input information and obtain output information, the control unit being configured to receive an initial weight, a target weight, and a food intake amount of the user via the user interface, the control unit being configured to generate the energy expenditure of the user, to generate the food intake amount and exercise instructions based on a difference between the user's initial weight and the user's target weight for display via the user interface, to receive the user's current weight via the user interface, and to generate a change in the user's weight, the control unit being configured to calibrate itself if the change in the user's weight does not correspond to an estimate made on the basis of the user's food intake amount and the user's energy expenditure by eliminating impact of at least one of errors caused by the user comprising incorrect input data entered by the user, levels of input data derived therefrom, and errors appearing in default settings made by the device, thereby modifying at least one of the food intake amount and the exercise instructions to be displayed via the user interface.

2. A device according to claim 1, wherein the device further comprises a heart rate measuring unit coupled to the control unit and measuring the user's heart rate, the control unit being configured to take into account the measured heart rate of the user when generating the user's energy expenditure.

3. A device according to claim 1, wherein the device further comprises an activity unit coupled to the control unit and measuring the physical activity of the user, the control unit being configured to take into account the user's physical activity when generating the user's energy expenditure.

4. A device according to claim 1, wherein the control unit is configured to generate a long-term average of the user's physical activity, the average being taken into account when food intake amount and exercise instructions are generated.

5. A device according to claim 1, wherein the control unit is configured to receive information defining the user's age over the user interface and to take into account the user's basal metabolic rate, defined on the basis of his age and weight, when generating the user's energy expenditure.

6. A device according to claim 1, wherein the control unit is configured to receive over the user interface information defining the user's workload and to take the user's workload into account when generating his energy expenditure.

7. A device according to claim 1, wherein the control unit is configured to generate a change in the user's weight on the basis of the user's current weight and his initial weight or current weight received and stored previously.

8. A device according to claim 1, wherein the control unit is configured to process the food amounts in terms of their energy contents.

9. A device according to claim 1, wherein the food intake amount instructions comprise a recommended energy content of a daily food intake amount.

10. A device according to claim 1, wherein the exercise instructions comprise recommended weekly exercising energy expenditure.

11. A device according to claim 1, wherein if the user's target weight is lower than his initial weight, the control unit is configured to determine for the user food intake amount instructions providing a daily food intake amount having an energy content that is lower than the user's daily energy expenditure and exercise instructions that increase the user's energy expenditure.

12. A device according to claim 1, wherein the control unit is configured to generate a long-term average of the change in the user's weight, the average being taken into account when food intake amount and exercise instructions are generated.

13. A device according to claim 1, wherein the control unit is configured to remind the user via the user interface to enter his current weight into the device via the user interface.

14. A device according to claim 1, wherein the control unit is configured to inform via the user interface the energy content of the food amount consumed within a predetermined period, the allowed total energy content determined for said predetermined period, and/or the difference between said total energy content and said energy content of the food amount consumed.

15. A device according to claim 1, wherein the control unit is configured to inform via the user interface the amount of energy expended in an exercise carried out within a predetermined period, the target exercise energy expenditure set for said predetermined period, and/or the difference between said target exercise energy expenditure and said expended energy amount.

16. A device according to claim 1, wherein the control unit is configured to prevent the energy content of the food intake amount instructions from dropping to a level that is too low and the energy content expended by applying the exercise instructions from increasing to a level that is too high.

17. A device according to claim 1, wherein the device is a part of a measuring device measuring energy expenditure in physical exercise.

18. A method of managing human body weight by using a portable, personal electronic device, the method comprising:
    receiving an initial weight and a target weight of a user via a user interface of the device;
    generating food intake amount and exercise instructions based on a difference between the user's initial weight and the user's target weight for display via the user interface;
    generating with the device the user's energy expenditure;
    receiving the user's food intake amount via the user interface;
    receiving the user's current weight via the user interface of the device;
    generating with the device a change in the user's weight; and
    calibrating the device if the change in the user's weight does not correspond to an estimate made on the basis of the user's food intake amount and the user's energy expenditure by eliminating impact of at least one of errors caused by the user comprising incorrect input data entered by the user, levels of input data derived therefrom, and errors appearing in default settings made by the device, thereby modifying at least one of the food intake amount and the exercise instructions to be displayed via the user interface.

19. A method according to claim 18, further comprising: taking into account the user's heart rate measured with the device, when generating the user's energy expenditure.

20. A method according to claim 18, further comprising: taking into account the user's physical activity measured with the device, when generating the user's energy expenditure.

21. A method according to claim 18, further comprising: generating with the device a long-term average of the user's physical activity, the average being taken into account when generating the food intake amount and exercise instructions.

22. A method according to claim 18, further comprising: receiving information defining the user's age via the user interface of the device and taking into account the user's basal metabolic rate, determined on the basis of his age and weight, when generating his energy expenditure.

23. A method according to claim 18, further comprising: receiving information defining the user's workload via the user interface of the device and taking the user's workload into account when generating his energy expenditure.

24. A method according to claim 18, further comprising: generating with the device a change in the user's weight, based on the user's current weight and his initial weight or current weight received and stored previously.

25. A method according to claim 18, further comprising: processing the food amounts in the device in terms of their energy contents.

26. A method according to claim 18, wherein the food intake amount instructions comprise a recommended energy content of a daily food intake amount.

27. A method according to claim 18, wherein the exercise instructions comprise recommended weekly exercising energy expenditure.

28. A method according to claim 18, further comprising: determining with the device food intake amount and exercise instructions for a user whose target weight is lower than his initial weight, the instructions providing a daily food intake amount having an energy content that is lower than the user's daily energy expenditure and exercise instructions increasing the user's energy expenditure.

29. A method according to claim 18, further comprising: generating with the device a long-term average of the change in the user's weight, the average being taken into account when food intake amount and exercise instructions are generated.

30. A method according to claim 18, further comprising: reminding the user via the user interface of the device to enter his current weight into the device via the user interface of the device.

31. A method according to claim 18, further comprising: informing via the user interface of the device the energy content of the food amount consumed within a predetermined period, the allowed total energy content determined for said predetermined period, and/or the difference between said total energy content and said energy content of the food amount consumed.

32. A method according to claim 18, further comprising: informing via the user interface of the device the amount of energy expended in an exercise carried out within a predetermined period, the target exercise energy expenditure set for said predetermined period, and/or the difference between said target exercise energy expenditure and said expended energy amount.

33. A method according to claim 18, further comprising: preventing with the device the energy content of the food intake amount instructions from being reduced to a level that is too low and the energy expenditure of the exercise instructions from increasing to a level that is too high.

34. A method according to claim 18, wherein the device is a part of a measuring device for measuring energy expenditure in physical exercise.

* * * * *